(12) United States Patent (10) Patent No.: US 8,610,768 B2
Holmberg et al. (45) Date of Patent: Dec. 17, 2013

(54) EYE DETECTION UNIT USING SEQUENTIAL DATA FLOW

(75) Inventors: Johnny Holmberg, Hallstahammar (SE); Peter Blixt, Hägersten (SE); John Elvesjö, Stockholm (SE)

(73) Assignee: Tobii Technology AB (SE)

( * ) Notice: Subject to any disclaimer, the term of this patent is extended or adjusted under 35 U.S.C. 154(b) by 371 days.

(21) Appl. No.: 12/833,575

(22) Filed: Jul. 9, 2010

(65) Prior Publication Data

US 2011/0013007 A1    Jan. 20, 2011

(30) Foreign Application Priority Data

Jul. 16, 2009 (EP) .................................... 09165653

(51) Int. Cl.
*H04N 7/18* (2006.01)

(52) U.S. Cl.
USPC ........................................................ 348/78

(58) Field of Classification Search
USPC ........................................................ 348/78
See application file for complete search history.

(56) References Cited

U.S. PATENT DOCUMENTS

| | | | | |
|---|---|---|---|---|
| 5,912,980 | A | 6/1999 | Hunke | 382/103 |
| 6,152,563 | A | 11/2000 | Hutchinson et al. | 351/209 |
| 2006/0093998 | A1* | 5/2006 | Vertegaal | 434/236 |
| 2006/0120599 | A1* | 6/2006 | Steinberg et al. | 382/167 |
| 2006/0291702 | A1 | 12/2006 | Miessbacher | 382/117 |
| 2007/0282506 | A1* | 12/2007 | Breed et al. | 701/45 |
| 2008/0231805 | A1 | 9/2008 | Schwerdtner | 351/210 |
| 2010/0195881 | A1* | 8/2010 | Orderud et al. | 382/131 |
| 2010/0272363 | A1* | 10/2010 | Steinberg et al. | 382/190 |

FOREIGN PATENT DOCUMENTS

| | | | |
|---|---|---|---|
| JP | 2008-206143 | 9/2008 | ............. H04N 5/335 |
| JP | 2009-89132 | 4/2009 | ............. H04N 5/335 |

OTHER PUBLICATIONS

Amir et al, "*An embedded system for an eye-detection sensor*" Computer Vision and Image Understanding, Academic Press, US, vol. 98, No. 1; Apr. 1, 2005 pp. 104-123.

* cited by examiner

*Primary Examiner* — David Czekaj
*Assistant Examiner* — Nam Pham
(74) *Attorney, Agent, or Firm* — Allen, Dyer, Doppelt, Milbrath & Gilchrist, P.A.

(57) ABSTRACT

The invention generally relates to systems and methods for eye detection for use in, for example, installations and systems for tracking eyes and gaze angle/directions. The system includes a plurality of eye detection units connected to an image sensor. The eye detection units are adapted to receive regions of picture elements of a digital image frame substantially in parallel and wherein the eye detection units are adapted to operate substantially in parallel, each eye detection unit being adapted to receive a specified region of the picture elements of at least one digital image frame and including an eye feature extraction module adapted to perform a eye feature extraction process on the received picture elements to identify predetermined eye features. An eye data generating module is adapted to receive information of potential identified eye features including picture element coordinates for the identified eye features, and the received region of picture elements, and generate eye data based on the information of potential eye features, wherein the eye data is generated if identified eye features fulfill predetermined conditions, and transfer generated eye data and the received regions of picture elements to a processing module, and wherein a data flow of the eye data and the region of picture elements of a digital image frame is substantially parallel.

24 Claims, 6 Drawing Sheets

*X-data:*

1 0 0 0 0 0 0 0 0
2 0 1 0 1 0 0 -1 -1
3 0 0 1 1 0 0 -1 0
4 0 0 0 1 0 0 0 0
   1 2 3 4 5 6 7 8

*Y-data:*

1 0 0 0 0 0 0 0 0
2 0 1 1 1 1 1 0 0
3 0 0 0 0 0 0 0 0
4 0 0 0 0 -1 -1 -1 0
   1 2 3 4 5 6 7 8

*Edge:*

EYE DETECTION UNIT USING SEQUENTIAL DATA FLOW

FIELD OF THE INVENTION

The invention generally relates to systems and methods for eye detection for use in, for example, installations and systems for tracking eyes and gaze angle/directions. Such a system can for example be used for observing or determining the position on a monitor or display at which a computer user is looking. There are a number of other conceivable applications and such other applications in which the present invention can be used include, inter alia, systems for analysing response on advertisement or systems for predicting driver vigilance and predicting drowsiness and sleep onset of, for example, vehicle drivers. The present invention can be realized as an embedded eye detection system that can be integrated in a computer such as a personal computer (PC) or a laptop. In particular, the present invention relates to eye detection systems and methods that offer reduced latency, reduced power consumption and increased frame rate in comparison to existing systems and that can be implemented in a programmable chip, for example, in a field-programmable gate array (FPGA), in a microprocessor, or in an application-specific integrated circuit (ASIC), or in a graphical processing unit (GPU).

BACKGROUND OF THE INVENTION

Monitoring or tracking eye movements and detecting a person's gaze point (as used herein, the point in space at which the person is looking) can be used in many different contexts. Such measurements can be an important information source in analysing the behaviour or consciousness of the person. It can be used both for evaluating the object at which the person is looking and for evaluating the respective person. The diverse uses of gaze point detection include studies on the usability of software and different types of interfaces; evaluation of web pages, advertising and advertisements; provision of means for educating pilots in simulator environments and for training surveillance personnel in security-critical roles; and research in psychology, behavioural sciences and human perception. A field which has attracted an increasing interest in recent years is the evaluation of advertising and other marketing channels. Eye-tracking information may then be gathered from a viewing test person's examination of advertising of particular merchandise, and the response of the test person is derived. Eye-tracking devices may also be used for collecting information on the response of the viewing person of the placement of a particular article on a shelf of a shop display.

One important area where eye tracking devices attracts a growing interest is interactive applications which employ information about the place at which a person is looking in order to respond or react in different ways. For example, by implementing an eye tracking device in a laptop the interaction possibilities between the user and the different software applications run on the computer can be significantly enhanced. By such implemented eye tracking device, a physically disabled person can for example interact with the computer by activating objects displayed on the screen by means of the eye and the gaze of the eye. Further, in an arcade game, the adventure experience of the game can be very much enhanced by this technique, for example, the user may direct a weapon using only his eyes.

Eye detection systems can also be employed in systems designed to monitor the attentiveness of a machine operator or drowsiness of drivers of a vehicle or aircraft, or a person working at a control console such as an air traffic controller.

Another example where eye detection systems can be useful is in conjunction with an identification system which employs iris patterns techniques.

It has been shown that real-time eye detection and eye-gaze tracking is important for many of the applications discussed above. Current commercial and research systems use software implementation and require a dedicated computer for the image-processing—a large, expensive, and complicated-to-use solution. Further, the eye detection systems of the current dedicated computers are inefficient in terms of use of computing power and power use. There is also a need of reducing the latency and increasing the frame rate in such eye detection systems. Therefore, large efforts have been put in to develop more accurate, power efficient and compact systems. In, for example, U.S. Pat. No. 5,859,686 a system and a method for finding and tracking the location of a subject's eye is disclosed. The system includes imaging apparatus that captures digitized images of a subject's face. The images are fed into an eye finding and tracking unit that processes each image to detect the position of the subject's eye and to track these eye positions over time. The eye finding and tracking unit identifies features within the image frame which exhibit attributes consistent with those associated with the appearance of a subject's eye and based on these features, a determination as to which of the potential eye locations that actually is an eye location. This is done by monitoring successive image frames to detect a blink. If a blink is detected at a potential eye location, it is deemed as an actual eye location. Hence, this system and method processes one image at a time and handles about 30 frames per second and may have difficulties to handle higher frame rates, or may require increased processing power to handle high frame rates, which also may result in an increased power consumption. Hence, this system suffers from a major bottleneck associated with the data processing rate. Another problem that may be encountered in the system and method according to U.S. Pat. No. 5,859,686 is that latencies between user action and the experienced response can occur due to the frame by frame handling of the image data, which is annoying for the user. Thus, this system and method do not satisfies the requirements regarding latency, computing efficiency, power consumption and frame rate of the today's user's.

In the article "An embedded system for an eye-detection sensor" by A. Amir et al., an image processing system and method for eye detection is presented. The system uses an FGPA for the image processing. The method for the eye detection is based on a subtraction scheme with two synchronized illuminators. Two frames are captured, one with on-axis illumination and the other with off-axis illumination. The illumination intensity of the off-axis frame is subtracted from the intensity of the on-axis frame to create a resulting binary image after thresholding. A connected component algorithm is used to detect pupils in this resulting image. This system processes one pair of images at a time, which introduces latencies and consumes extra power.

Thus, there is a need within the art of improved eye detections systems for implementation in a computer and, in particular, there is a need for such eye detection systems that provides increased frame rate, reduced power consumption and reduced latency in comparison to existing systems.

SUMMARY OF THE INVENTION

An object of the present invention is to provide eye detection systems and methods that offer reduced latency, reduced power consumption and increased frame rate in comparison to existing systems.

A further object of the present invention is to provide eye detection systems and methods for implementation in a computer such as a laptop that offer reduced latency, reduced power consumption and increased frame rate in comparison to existing systems.

Another object of the present invention is to provide eye detection systems and methods for implementation in a computer that can be used with standard components of the computer including e.g. a web camera.

Yet another object of the present invention is to provide an embedded eye detection system that can be integrated in a computer such as a personal computer (PC) or a laptop.

Still another object of the present invention is to provide an eye detection system that can be implemented in a programmable chip, for example, in a field-programmable gate array (FPGA), in a microprocessor, or in an application-specific integrated circuit (ASIC).

Another object of the present invention is to provide an eye detection system that can be implemented on a graphical processing unit (GPU).

These and other objects of the present invention will become apparent from the specification and claims together with the appended drawings.

In the context of the present application, the term "subset" refers to amounts of the picture elements of a picture ranging from an empty amount, i.e. zero picture elements, to all picture elements of the picture. In a typical case, the subset may include one or a number of columns or rows. Further, different subsets may be adjacent to each other, i.e. edge to edge, or may overlap each other.

According to a first aspect of the present invention, there is provided an eye detection system comprising at least one illuminator element adapted to emit light in a direction towards the head of a user and at least one image sensor being adapted to receive light from the illuminated head of the user and repeatedly capture pictures, each being represented by a digital image frame comprising a matrix of picture elements. The system further includes a plurality of eye detection units connected to the image sensor, the eye detection units being adapted to receive regions of picture elements of a digital image frame substantially in parallel and wherein the eye detection units are adapted to operate substantially in parallel, each eye detection unit being adapted to receive a specified region of the picture elements of at least one digital image frame and including an eye feature extraction module adapted to perform a eye feature extraction process on the received picture elements to identify predetermined eye features, and an eye data generating module connected to the eye detection units. The eye data generating module is adapted to: receive information of potential identified eye features from the eye detection units, the information including picture element coordinates for the identified eye features, and the received region of picture elements, and generate eye data based on the information of potential eye features, wherein the eye data is generated if identified eye features fulfil predetermined conditions, and transfer generated eye data and the received regions of picture elements to a processing module, and wherein a data flow of the eye data and the region of picture elements of a digital image frame is substantially parallel.

The illuminator elements may be controlled of a processing unit in which the eye data is processed to, for example, count the number of glints. The processing unit may also be adapted to control the image sensor to forward, for example, a selected subset of the picture elements in which an eye was identified in a previous picture. However, in embodiments of the present invention, the image sensor is controlled by the eye data generating module to forward, for example, a selected subset of the picture elements in which an eye was identified in a previous picture. The processing unit may, for example, be integrated in a CPU of a computer such as a PC or laptop.

According to a second aspect of the present invention, there is provided an eye detection system includes a plurality of eye detection units connectable to an image sensor, the eye detection units being adapted to receive regions of picture elements of a digital image frame substantially in parallel and wherein the eye detection units are adapted to operate substantially in parallel, each eye detection unit being adapted to receive a specified region of the picture elements of at least one digital image frame and including an eye feature extraction module adapted to perform a eye feature extraction process on the received picture elements to identify predetermined eye features, and an eye data generating module connected to the eye detection units. The eye data generating module is adapted to: receive information of potential identified eye features from the eye detection units, the information including picture element coordinates for the identified eye features, and the received region of picture elements, and generate eye data based on the information of potential eye features, wherein the eye data is generated if identified eye features fulfil predetermined conditions, and transfer generated eye data and the received regions of picture elements to a processing module, and wherein a data flow of the eye data and the region of picture elements of a digital image frame is substantially parallel.

According to a third aspect of the present invention, there is provided a method for detecting an eye using a eye detection system according to the first or second aspect of the present invention. The method comprises the steps of sending selected subsets of picture elements of a digital image frame substantially in parallel from an image sensor to a plurality of eye detection units, performing parallel eye feature extraction processes on the received picture elements to identify predetermined eye features in the selected subsets in eye feature extracting modules, sending information of potential identified eye features from the eye detection units, the information including picture element coordinates for the identified eye features, and the received region of picture elements to an eye data generating module, and generating eye data based on the information of potential eye features, wherein the eye data is generated if identified eye features fulfil predetermined conditions, and transferring generated eye data and the received regions of picture elements to a processing module, and wherein a data flow of the eye data and the region of picture elements of a digital image frame is substantially parallel.

The present invention is thus based on the idea of processing subsets of the picture elements of picture captured by means of a photo-sensor in parallel and substantially simultaneously in parallel eye detection units. The subsets may overlap or may be edge to edge and may comprise one or more columns and/or one or more rows. Hence, the image captured by the sensor is divided in a multiple one-dimensional data flows, either row or column wise, and each data flow is processed individually and in parallel in respective eye detection units. In respective eye detection unit, candidate eye features, for example, (or potential) glints and/or pupils are extracted and forwarded to the eye data generating module. The eye feature extraction process includes sequentially determining whether adjacent picture elements should be connected to an object, or potential eye feature, which sequential determination is performed column wise or row wise. Temporal buffering of picture element identified in a row (or column) is used to compare picture elements of a present row with picture elements of a preceding row in which potential eye features have been identified to connect picture elements in different rows (or columns) to thereby create continuous objects (i.e. potential eye features) spanning over more than one row and/or column in the analysed subset of the digital image frame. The eye data generating module determines which of the candidates (i.e. potential eye features including for example an eye or a glint) that satisfy predetermined conditions and thus actually constitutes for example glints or an eye. When an eye feature (e.g. eye or a glint) has been identified and verified, eye data including e.g. picture element coordinates for the identified eye or glint is forwarded to a processing unit. The processing unit may use this eye data to determine, for example, a gaze direction or to count the number of glints.

This inventive concept provides several advantages. For example, due to the eye detection units operating in parallel, where each processes only a subset of the picture elements, and due to that eye data is generated and forwarded to processing only if a potential eye or a potential glint have been identified, reduced latency, reduced power consumption and increased frame rate can be achieved in comparison to existing systems. Further, the system and method of the present invention can be implemented in, for example, a GPU of a computer such as a PC or a laptop offering reduced latency, reduced power consumption and increased frame rate in comparison to existing systems. The present invention can also be used with standard components of the computer including e.g. a web camera. In particular, the system of the present invention can be realized as an embedded eye detection system that can be integrated in a computer such as a laptop. The eye detection system or parts or components of the eye detection system according to the present invention, for example, the eye detection units and the eye data generating module can be implemented in a programmable chip, for example, in a field-programmable gate array (FPGA), in a microprocessor, or in an application-specific integrated circuit (ASIC) or on a graphical processing unit (GPU).

In an embodiment of the present invention, the eye data generating module is adapted to feedback information to the sensor about the positions where an eye(-s) and/or glints have been found in previous image frames to select the portion of the light sensitive surface of the sensor that is to be exposed before each new picture is taken or to be used in each new picture and controls the sensor in accordance therewith. Further, the sensor may be instructed to forward only subsets of such a selected portion to the eye detection units and for the glint and/or pupil extraction process. If the user's eye(-s) is(are) and/or glints are found in the preceding picture only a small portion of the picture elements of the light sensitive surface of the sensor is used. Thereby, the power generation can be significantly reduced. Only in the case where no eye or no glints have been found, data from all picture elements of the light sensitive surface of the sensor is forwarded to the eye detection units. Thereby, the processing load may be reduced even further and the sampling velocity can be improved even further. Alternatively, or as a compliment, the eye data generating module may be adapted to feedback amplitude information of the intensity values of an detected eye(-s) or a detected glint(-s) to the sensor. The eye data generating module hence uses information of the amplitude values of identified eyes or glints of previous pictures to select the portion of the light sensitive surface of the sensor that is to be exposed before each new picture to be taken or to be used in each new picture and controls the sensor in accordance therewith. For example, an amplitude threshold may be set such that only regions including picture elements having an intensity value above a predetermined amplitude threshold are selected for exposure before a new picture is taken or are used in a new picture. In another example, amplitude thresholds, e.g. an amplitude interval defined by upper and lower amplitude limits, are set such that only regions including picture elements having an intensity value within a predetermined amplitude interval are selected for exposure before a new picture is taken or are used in a new picture.

As the skilled person realizes, steps of the methods according to the present invention, as well as preferred embodiments thereof, are suitable to realize as computer program or as a computer readable medium.

These and other aspects of the invention will be apparent from and elucidated with reference to the embodiments described hereinafter. All terms used herein are to be interpreted according to their ordinary meaning in the technical field, unless explicitly defined otherwise herein.

BRIEF DESCRIPTION OF THE DRAWINGS

Embodiments of the present invention will be described with reference to the accompanying drawings, on which.

DETAILED DESCRIPTION OF EMBODIMENTS OF THE INVENTION

The present invention relates to eye detection systems and methods. The embodiments disclosed herein are merely exemplary or representative of the present invention. The present invention is not to be limited to the specific disclosures presented herein.

Figure 1:
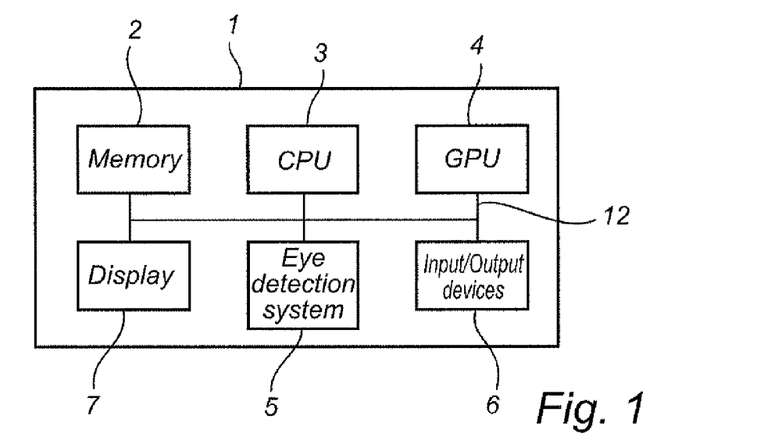
FIG. 1 is a functional block diagram of an exemplary device in which the present invention may be implemented.
Figure 2:
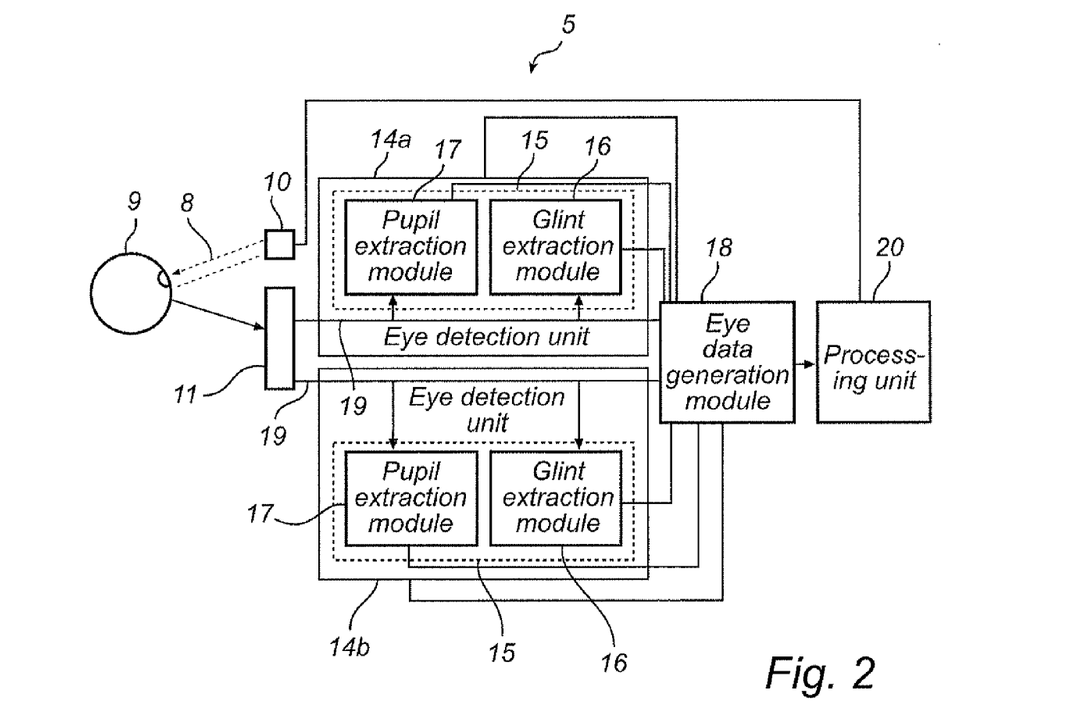
FIG. 2 schematically illustrates an eye detection system according to an embodiment of the present invention.

With reference first to FIGS. 1 and 2, an eye detection system according to the present invention implemented in a computer will be discussed. The system is, for example, capable of determining the point on a monitor or screen at which the computer user is looking/gazing. The determination of the point on a monitor or screen at which the computer user is looking/gazing is performed by tracking the eyes of the user and in particular by determining the gaze angles of the eyes and the position of the eye relatively the monitor. However, the algorithms for the tracking of the eyes and for the determining the gaze angles is not part of the present invention and will not be described in detail herein. The eye detection system 5 is in this embodiment implemented in a computer such as a laptop, or a personal computer (PC). The eye detection system 5 according to the present invention, or parts or components of the system, for example, the eye detection units and the eye data generating module can be implemented in a programmable chip, for example, in a field-programmable gate array (FPGA), in a microprocessor or CPU of the computer, or in an application-specific integrated circuit (ASIC) or in the graphical processing unit (GPU) of the computer or in a complementary metal-oxide-semiconductor (CMOS) sensor.

FIG. 1 shows a functional block diagram of such an exemplary device in which the present invention may be implemented. The device 1 may include memory 2, central processing unit (CPU) 3, graphics processing unit (GPU) 4, an eye detecting system 5 according to the invention, input/output devices 6, display screen 7. Further, the device 1 also includes communications interface 12, this may e.g. be RS-232, Universal Serial Bus (USB) or a controller-area network (CAN). The memory 2 may include static memory, such as a read only memory (ROM), and/or dynamic memory, such as a random access memory (RAM), video RAM, or onboard cache, for storing data and machine-readable instructions. Memory 2 may also include storage devices such as a floppy disc, CD ROM, CD read/write (R/W) disc, and/or flash memory as well as other types of storage devices.

The CPU may include one or more processors, microprocessors, and/or processing logic capable of controlling the device 1. The GPU 4 may include a graphics rendering device, such as dedicated graphics card and/or integrated graphics processor that may use a portion of the memory 2. The GPU may perform computation, manipulation and display of graphics and may, for example, control the brightness, resolution, and refresh rates of the display screen 7. The input/output devices 6 may include a printer, a keyboard, mouse, speaker, digital camera, light emitting diodes etc.

The eye detection system 5 may use the input/output device 6, for example, to emit NIR light towards the head of a user and to capture pictures of the head of the used. As an alternative, the eye detection system 5 may include at least one illuminator element and a photo-sensor or a digital camera. The eye-detection system may use the CPU or the GPU for feature extraction and image processing. Especially the GPU is suitable for parallel processing due to the numerous processing cores.

Referring now to FIG. 2, the eye detection system 5 according to the present invention will be described.

At least one illuminator element or light source 10, e.g. a NIR diode, is adapted to emit light 8 in a direction towards the head 9 of a user and is mounted, for example, at the upper edge of the monitor. In this embodiment, the illuminator element 10 is included in the system but it is also conceivable to use existing components of the computer, for example, a NIR diode. A control unit of the system may control the switching of the NIR diode on and off.

Furthermore, at least one photo-sensor 11 provided with an optical system (not shown) may, for example, be mounted at the center of the bottom edge of the monitor. The optical system may be located in front of the photo-sensor for filtering away undesired light and for focusing a picture on the light sensitive surface of the photo-sensor 11. The photo-sensor 11 receives light from the illuminated head of a user and repeatedly captures pictures, where each picture is represented by a digital image frame comprising a matrix of picture elements or pixel elements. Hence, digital image frames including the face and the eyes of the user are produced. Each digital frame comprises an array of pixel values or picture elements representing the intensity of light from the illuminated face of the user. These pixel values representing the received intensity are located in the array specified by x and y coordinates. According to this invention, blocks or subset of the picture elements is forwarded in parallel data flows to the eye finding process, as will be described hereinafter. Each subset may contain a row, a column, a number of rows, or a number of columns. Further, the rows or columns of adjacent subsets may overlap such that the same row or column (or rows or columns) are forwarded to processing in more than one parallel data flows or they may be edge to edge.

If more than one illuminator element is used, they may be located such that at least one illuminator element is arranged in close proximity to or coaxially with an optical axis of the photo-sensor 11. Other illuminator elements 10 are arranged at a larger distance from the optical axis. By illuminating the elements 10 being placed in close proximity to or coaxially with the optical axis of the photo-sensor 11, an easy observable bright eye effect of the pupil or pupils can be caused while illumination of the other illuminator (-s) 10 causes reflections from the cornea without causing any easy observable bright eye effect. In a picture captured with bright eye effect, the pupil is illuminated and the reflection from the illuminator element 10 from the cornea is seen as a point-shaped reflection. Further, there is a large contrast between the image fields that correspond to the pupil and iris and therefore the boundary line between these two fields can be calculated with good accuracy. In the determination of the center, adaptation of an ellipse to the boundary line can be used, which is particularly important in the case where the pupil is only partly visible in the picture. By determining a vector from the center of the reflection from the illuminator element 10 and the center of the pupil can be used to determine the gaze direction. In pictures obtained by means of the illuminators 10 arranged at a larger distance from the sensor, there will be a relatively low contrast between the image fields that correspond to different portions of the eye. However, in these pictures, the direct reflections from the illuminator elements appear very clearly. The positions and the distances between the different reflections can be determined and evaluated to determine the distance of the eye from the sensor.

The system 5 further comprises a plurality of eye detection units 14 connected to the photo-sensor in parallel. One or several data buses 19 may be arranged to transfer picture element data from the image sensor 11 to the eye detection units 14.

In FIG. 2, only two eye detection units 14a and 14b are shown, but, however, the number of eye detection units 14a, 14b may vary depending on, for example, the specific application and the requirements with regard to latency, power consumption, etc. Each eye detection unit 14a, 14b is adapted to receive at least a subset of the picture elements of a digital image frame from the sensor 11, which subset as mentioned above may be a one-dimensional part of the picture elements e.g. a row or a column. The subsets may also overlap each other.

Each eye detection unit 14a, 14b includes an eye feature extracting module 15 adapted to perform a eye feature extraction process on the received picture elements to identify picture elements including predetermined eye features such a part of a glint, a portion of the iris or a part of a pupil. In other words, the eye feature extracting module 15 detects or identifies regions of picture elements of significant difference in the received subsets of the digital image frames. The eye feature extracting module 15 is adapted to process each intensity value of the picture elements of a received subset of picture elements, sequentially determine whether adjacent picture elements of a row or a column of the subset of picture elements are correlated by comparing the processed intensity value of the picture elements, wherein picture elements are determined to be correlated if the respective processed intensity value fulfils predetermined conditions. Further, the eye feature extracting module 15 is adapted to determine whether correlated elements in a row or a column is correlated with elements of a former row or a column, respectively, connect such correlated elements into sub-regions of elements, and determine such sub-regions to include potential eye features. This process will be described in more detail below.

In one embodiment, the eye feature extracting module 15 comprises a glint extraction module 16 and a pupil extraction module 17.

The glint extraction module 16 is adapted to perform a glint extraction process on the received picture elements to identify picture elements including at least a part of a potential glint of an eye of the user. A glint is a small bright object and the edge of the glint is usually steep, which entails that edge detection is a suitable method for identifying a glint. The glint extraction module is adapted to perform edge calculation to determine edge values of the respective picture elements of a received subset of picture elements. Further, it is sequentially determined whether adjacent picture elements of a row or a column of the subset of picture elements are correlated by comparing the respective edge value, wherein picture elements are determined to be correlated if the edge value is the same, and it is determined whether correlated elements in a row or a column is correlated also with elements of a former row or a column, respectively. Moreover, the glint extraction module 16 is adapted to connect such correlated elements into sub-regions of elements and to determine such sub-regions to be a potential glint. The glint extraction process will be described in more detail below with reference to FIGS. 3-6.

The pupil extraction module 17 is adapted to perform a pupil region extraction process on the received picture elements to identify picture elements including at least a part of a potential pupil region of an eye of the user. In embodiment of the present invention, a picture element having an intensity value within a predetermined range of values is determined to be a part of a potential pupil. Specifically, the pupil extraction module is adapted to sequentially determine whether adjacent picture elements of a row or a column of the received subset of picture elements are correlated by comparing the respective intensity value, wherein two elements are determined to be correlated if the intensity values are within a predetermined interval (in one embodiment if the intensity values are the same). Further, the pupil extraction module 17 is adapted to determine whether correlated elements in a row or a column is correlated with elements of a former row or column, respectively, connect such correlated elements into sub-regions of elements, and to determine such sub-regions to be at least a potential pupil. The pupil extraction process will be described in more detail below with reference to FIG. 7.

An eye data generating module 18 is connected to the glint extraction module 16 and/or the pupil extraction module 17 and is adapted to generate eye data using identified potential pupils and/or glints, wherein the eye data is generated if identified eye features fulfil predetermined conditions. In one embodiment, the eye data generating module 18 is adapted to map sub-regions determined to be at least a part of a potential pupil and sub-regions determined to be a potential glint to establish whether there is an overlap or close relation in distance, and if such an overlap or close relation in distance is established between at least a part of a potential pupil and at least one glint, to determine that the sub-regions including the at least a part of a potential pupil and the at least one glint constitute an eye. Thus, only when an eye has been identified among the potential pupils and glints, eye data is generated and forwarded to a processing unit 20. Thus, the processing load of the processing unit 20 can be reduced since only a small region around a pupil and glint needs to be analyzed to determine, for example, gaze direction. In an alternative embodiment, only information about glints are forwarded to the processing unit 20, for example, to identify glints to determine the degree of eye-closure. In this case, only a small region around the glints needs to be analyzed.

Figure 8:
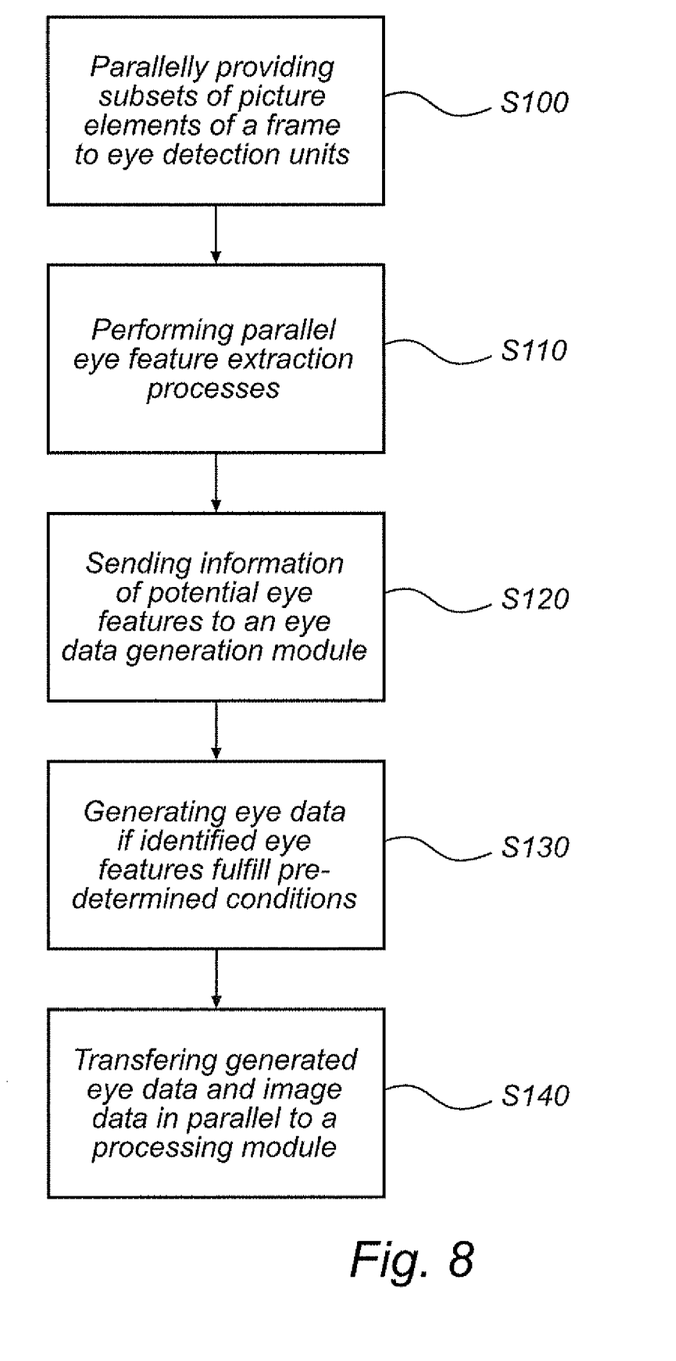
FIG. 8 shows the general steps of the eye detection method according to the present invention.

Thus, the basic idea of the present invention is to select subsets or regions of the picture elements of the sensor surface and process each subset individually and in parallel in the eye detection units. The subsets may overlap or may be edge to edge and may comprise one or more columns and/or one or more rows. Hence, the image captured by the sensor is divided in a multiple one-dimensional data flows, either row or column wise, and each data flow is processed individually and in parallel in the eye detection units. In respective eye detection unit, candidate (or potential) glints and/or pupils are extracted and forwarded to the eye data generating module which determine which of the candidates that satisfy predetermined conditions and thus constitutes e.g. glints or an eye. When an eye or a glint has been identified and verified, eye data including e.g. picture element coordinates for the identified eye or glint is forwarded to a processing unit. The processing unit may use this eye data to determined, for example, a gaze direction or to count the number of glints. The general steps of the method for detecting an eye using an eye detection system according to the present invention is illustrated in FIG. 8. The method comprises the general steps of:

S100: providing selected subsets of picture elements of a digital image frame in parallel to a plurality of eye detection units;

S110: performing parallel eye feature extraction processes on the received picture elements to identify predetermined eye features in said selected subsets in eye feature extracting modules;

S120: sending information of potential identified eye features from said eye detection units, said information including picture element coordinates for said identified eye features, and the received region of picture elements to an eye data generating module;

S130: generating eye data based on said information of potential eye features, wherein said eye data is generated if identified eye features fulfil predetermined conditions; and S140: transferring generated eye data and the received regions of picture elements, i.e. the image data, in parallel to a processing module, and wherein a data flow of said eye data (i.e. a verified eye feature which may be an eye or a glint) and the region of picture elements of a digital image frame is substantially parallel. Thus, when an eye or a glint has been identified and verified, eye data including e.g. picture element coordinates for the identified eye or glint is forwarded to a processing unit. The processing unit may use this eye data to, for example, count the number of glints and/or pupils.

Figure 3:
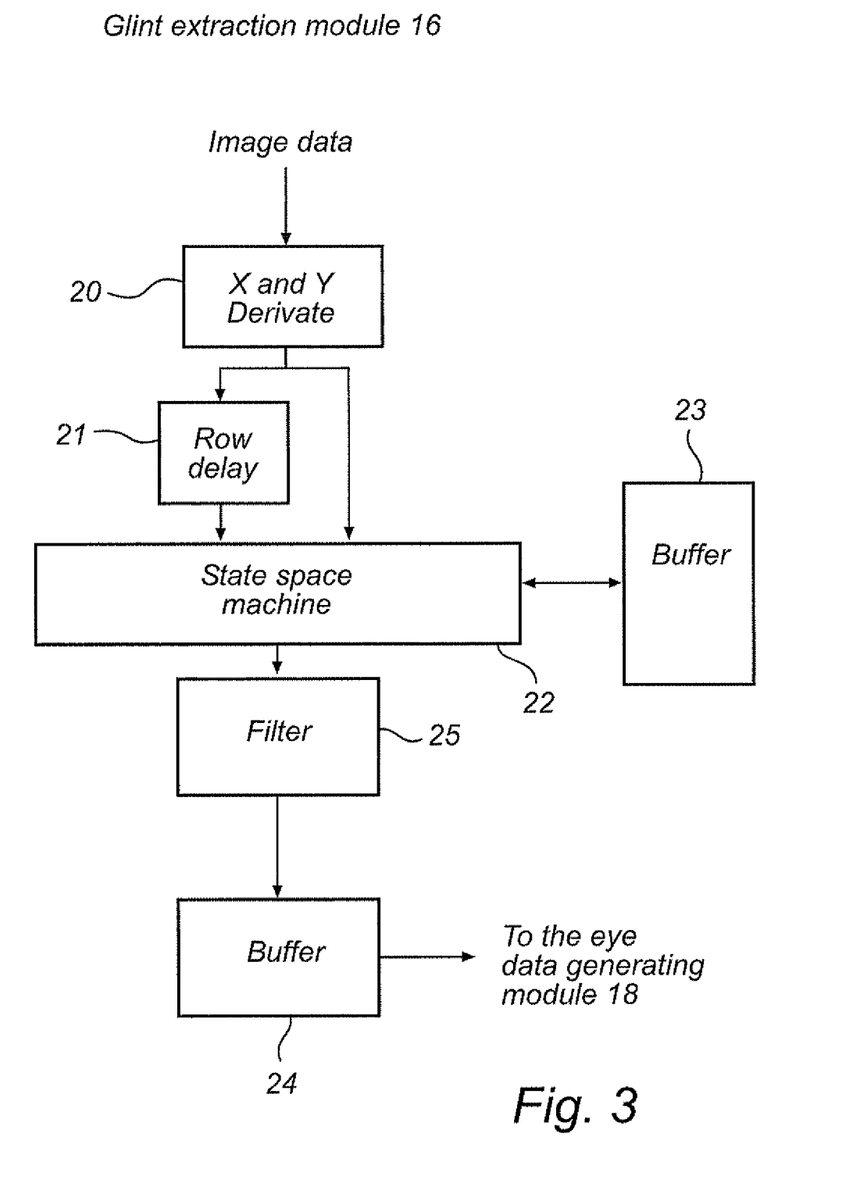
FIG. 3 schematically shows an embodiment of a glint extraction module in accordance with an embodiment of the present invention.

With reference now to FIG. 3, the glint extraction module 16 will now be described in more detail. A subset of a digital image frame is received at a derivative calculation module 20 adapted to calculate the intensity derivative in the x- and y-direction. The derivatives are calculated using two or more points in one direction or using a kernel as in Sobel or Prewitt gradient calculations. In the context of the present invention, the glints are small and have equal edge properties around at least a part of it. The edge calculations are implemented for separate x- and y-direction.

The edge values are first compared with a predetermined threshold. If the value is greater than this threshold, the position [x,y] where the edge value was calculated will be set to an edge. The sign of the edge is also stored. The edge calculation delivers if an edge has been detected and the sign of the edge both for x- and y-directions. From the edge detection a ternary (or trinary) picture (including the values −1, 0, 1) is obtained containing information about the edges of the original picture. Information about the direction of the edges and signs are also obtainable. This data is used to find where the glints are in the picture. The edge finding algorithm can use more elaborate schemes having multiple threshold values for gradients and logical statements to determine if the candidate has the expected shape. This is crucial for sorting out glints from glasses, the sclera, jewellery, etc. Glass glints are usually more elongated than glints from the cornea.

Figures 4, 5:
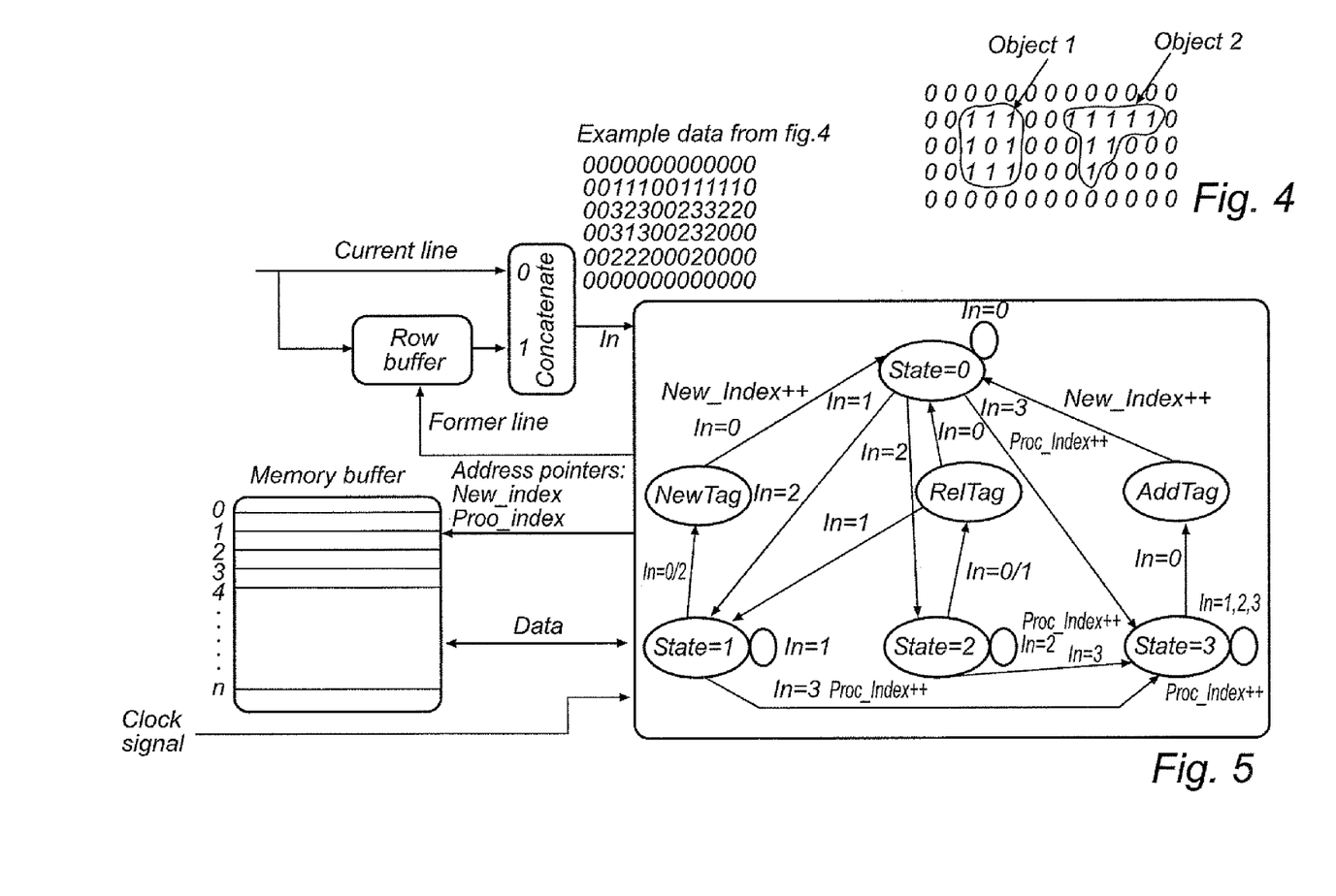
FIG. 4 illustrates examples of the picture element handling process in the glint extraction module.
FIG. 5 schematically shows a part of the glint extraction module in accordance with an embodiment of the present invention.
Figure 6:
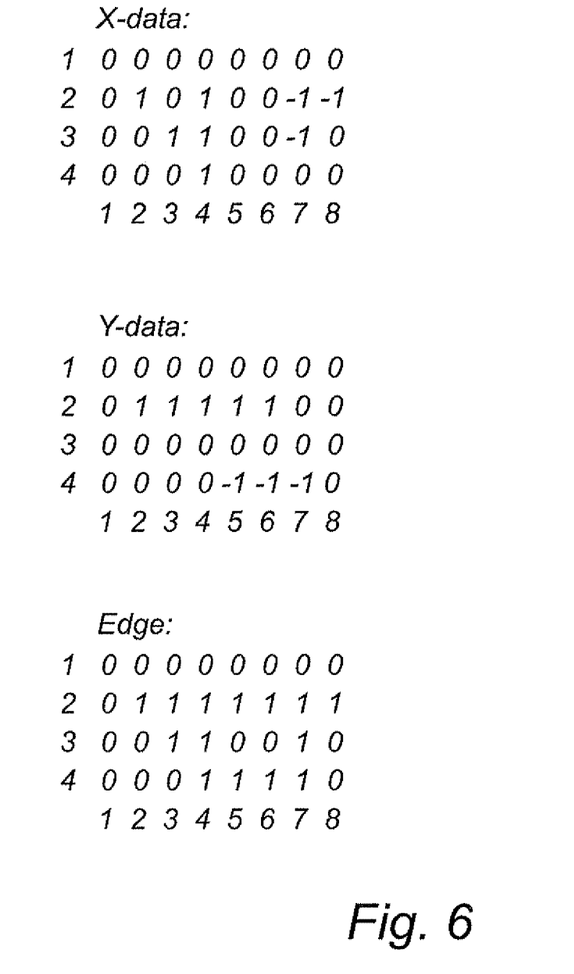
FIG. 6 illustrates examples of the picture element handling process in the glint extraction module.

According to the present invention, a connected component algorithm is used to find objects in a binary picture that are connected to each other. The binary image is obtained by taking absolute values of the ternary image. That is, if a ternary pixel with the (absolute) value of one (marks an edge) is located next to another one valued pixel then they are merged into one new object with the combined features. Due to the parallel flow of subsets of picture elements to the eye detection units, the whole picture is not obtainable at the same time which makes the administration of the data difficult, which however is solved by the present invention. In FIG. 4, an example of a binary picture with two objects that have been connected by a number of identified items, i.e. binary ones, is shown.

The binary picture is forwarded to a row delay unit 21 and a state space machine 22 for a connection process. The connection process is performed on the received picture elements to determine whether an identified item on a current row is connected to an item on a former row (or column). A region of such connected items is a potential glint. Referring to FIG. 4, two such regions of connected items are shown, object 1 and object 2. In the connection process, information of the former row is stored in a row buffer 21 and together with the information of the current row the state space machine 22 determines whether an identified item, i.e. a binary one, is connected to an item of the former row. In FIG. 5, a schematic detailed view of the state space machine 22, and the buffer 23 is shown. Note that the example from the FIG. 4 is used to explain the concatenation of the current and former rows. The state machine 22 according to this embodiment consists of 7 states, where there of the states (AddTag, NewTag, RelTag) occur instantly while the other are controlled by clock signal from a data flow clock (not shown), for example, the image sensor's. However, it should be noted that the state machine described with reference to FIG. 5 is exemplary and for illustrative purposes.

The pupil estimation part performed in the eye-data generating module 18 requires position and geometrical data of glint and pupil candidates, e.g. the center of the glint and pupil, size, circularity, and contrast value. To explain these parameters, reference is being made to FIG. 6. It is connected to one object since each 1 boarder to another 1. Based on this, geometrical features of the glint and pupil candidates are calculated, such as radius at different thresholds, circularity, size, centroid. Another feature calculated is the contrast value.

Thereafter, the objects, i.e. potential glints, identified in the process described above can be forwarded to the eye data generating module 18 where a check is performed whether identified potential glints and a potential pupil, identified in the pupil extraction process that will be described below, constitutes an eye.

Figure 7:
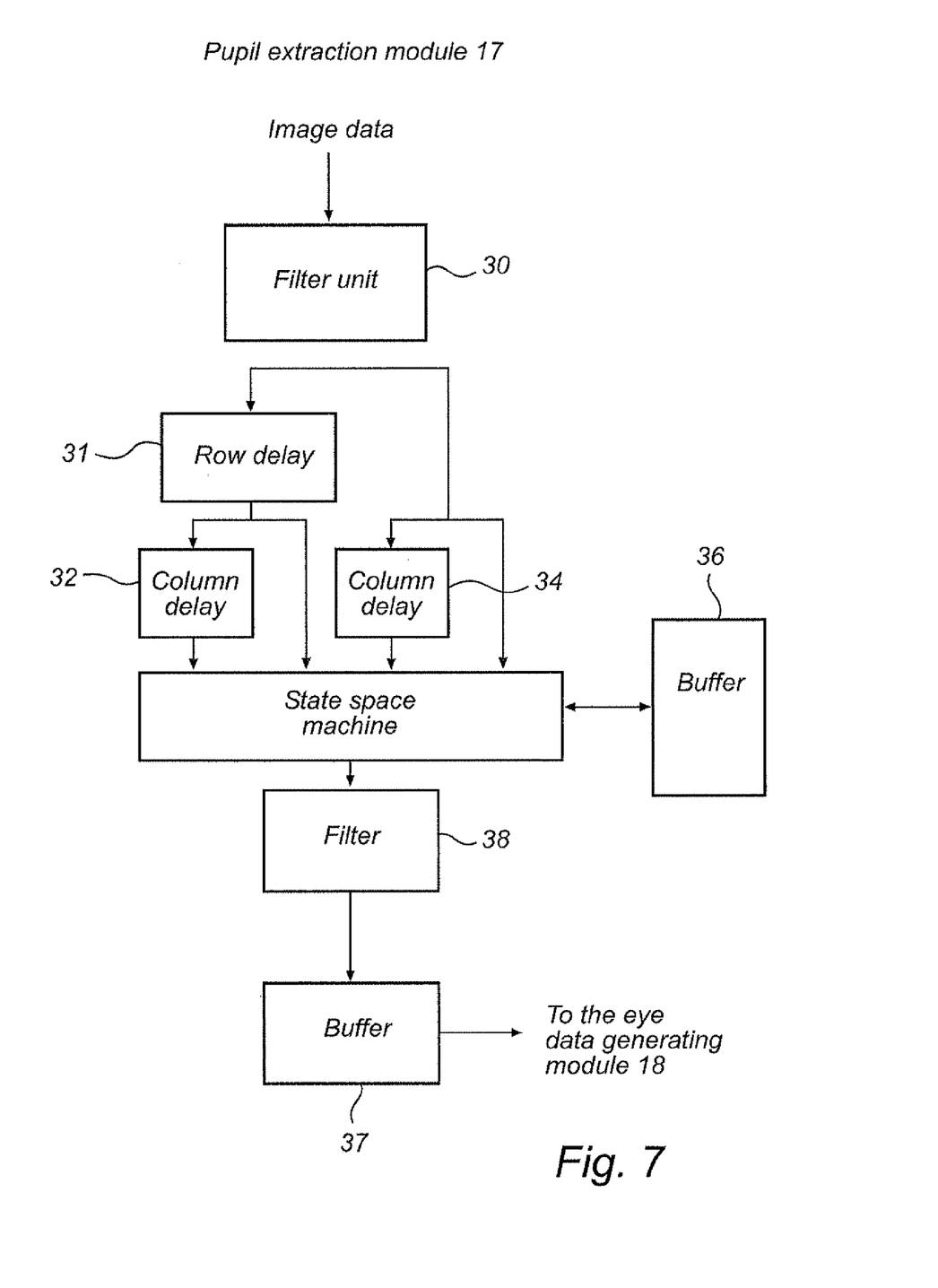
FIG. 7 shows an embodiment of a pupil extraction module in accordance with an embodiment of the present invention.

With reference now to FIG. 7, the pupil extraction module 17 will be described. The principles for the pupil extraction process are similar to the glint extraction process. However, we will briefly discuss the pupil extraction module 17 below. Image data, i.e. a subset of a digital image frame, is received at a filter unit 30 where the received picture elements, each including an intensity value, are filtered in different filtering steps. In one embodiment, the received picture elements are processed in three different filtering steps. First, the picture elements are filtered in a FIR-filter (Finite Impulse Response filter) unit in order to reduce the noise. The signal components of the pupil have a relatively low frequency and, therefore, signal components having a high frequency are filtered off in the FIR-filter. In this embodiment, the FIR-filter is a 1-dimensional filter of $20^{th}$-order. Thereafter, the picture elements are filtered in a non-linear filter, where sub-sections of the subset are processed such lower values successively is removed in case of an image captured at bright pupil conditions, or such that higher values are removed successively in case of an image captured at dark pupil conditions. Then, the picture elements are processed in a homogenization filter including a quantization procedure. After the filtering process, the filtered subset of the picture elements are transferred to a row delay unit 31 and column delay units 32, and 34. In the state space machine 35, a similar procedure to connect neighbouring picture elements as have been described above in connection with the glint extraction procedure is performed. In this case, objects (i.e. adjacent picture elements) having the same intensity value level are identified. The potential objects are temporarily stored in the buffer 36. When the objects are released and stored in the buffer 37 (after being filtered at the filter unit 38), each objects is defined by intensity value and coordinate data in the x-direction and the y-direction (X-start, Y-start, X-end, and Y-end).

Thereafter, the objects, i.e. potential pupils, identified in the process described above can be forwarded to the eye data generating module 18 where a check is performed whether identified potential glints and a potential pupil constitutes an eye.

According to an embodiment of the present invention, the eye data generating module 18 is adapted to feedback information to the sensor 11 about the positions where an eye(-s) and/or glints have been found in previous image frames to select the portion of the light sensitive surface of the sensor 11 that is to be exposed before each new picture is taken or to be used in each new picture and controls the sensor 11 in accordance therewith. Further, the sensor may be instructed to forward only subsets of such a selected portion to the eye detection units 14a and 14b for the glint and/or pupil extraction process. If the user's eye(-s) is(are) and/or glints are found in the preceding picture only a small portion of the picture elements of the light sensitive surface of the sensor 11 is used. Only in the case where no eye or no glints have been found, data from all picture elements of the light sensitive surface of the sensor 11 is forwarded to the eye detection units 14a, 14b. Thereby, the processing load may be reduced even further and the sampling velocity can be improved even further. Alternatively, or as a compliment, the eye data generating module 18 may be adapted to feedback amplitude information of the intensity values of an detected eye(-s) or a detected glint(-s) to the sensor 11. The eye data generating module 18 hence uses information of the amplitude values of identified eyes or glints of previous pictures to select the portion of the light sensitive surface of the sensor 11 that is to be exposed before each new picture to be taken or to be used in each new picture and controls the sensor 11 in accordance therewith. For example, an amplitude threshold may be set such that only regions including picture elements having an intensity value above a predetermined amplitude threshold are selected for exposure before a new picture is taken or are used in a new picture.

In another example, amplitude thresholds, for example, an interval are set such that only regions including picture elements having en intensity value within a predetermined amplitude interval are selected for exposure before a new picture is taken or are used in a new picture.

While the invention disclosed herein has been described by means of specific embodiments and applications thereof, numerous modifications and variations could be made therein by those skilled in the art without departing from the scope of the inventions, which is defined by the appended claims.

The invention claimed is:

1. An eye detection system comprising:
   at least one illuminator element adapted to emit light in a direction towards the head of a user;
   at least one image sensor being adapted to receive light from the illuminated head of a user and repeatedly capture pictures, each being represented by a digital image frame comprising a matrix of picture elements;
   a plurality of eye detection units connected to said image sensor, said eye detection units being adapted to receive a selected data flow including at least one row or column of picture elements of a digital image frame, said digital frame being divided in multiple data flows, substantially in parallel from said image sensor and wherein said eye detection units are adapted to operate substantially in parallel, each eye detection unit being adapted to receive a selected data flow of the picture elements of at least one digital image frame and including an eye feature extraction module adapted to perform a eye feature extraction process on the received picture elements to identify predetermined eye features; and
   an eye data generating module connected to said eye detection units and being adapted to:
      receive information of potential identified eye features from said eye detection units, said information including picture element coordinates for said identified eye features, and the received region of picture elements,
      generate eye data based on said information of potential eye features, wherein said eye data is generated if identified eye features fulfil predetermined conditions, and
      transfer generated eye data and the received regions of picture elements to a processing module, and wherein a data flow of said eye data and the region of picture elements of a digital image frame is substantially parallel; and
   said eye feature extraction module comprising a glint extraction module adapted to perform a glint extraction process on the received picture elements to identify picture elements including at least a part of a potential glint of an eye of the user, with said glint extraction module being configured to
      determine edge values of the respective picture elements of a received subset of picture elements, and
      determine a potential glint by connecting picture elements of the subset having correlated edge values.

2. The eye detection system according to claim 1, wherein said eye feature extraction module is adapted to:
   process each intensity value of the picture elements of a received data flow of picture elements;
   sequentially determine whether adjacent picture elements of a row or column of the data flow of picture elements are correlated by comparing the processed intensity value of said picture elements, wherein picture elements are determined to be correlated if the respective processed intensity value fulfils predetermined conditions;
   determine whether correlated elements in a row or a column are correlated with elements of a former row or column, respectively;
   connect such correlated elements into sub-regions of elements; and
   determine such sub-regions to include potential eye features.

3. The eye detection system according to claim 1, wherein said glint extraction module is adapted, in said glint extraction process, to:
   perform an edge calculation to determine edge values of the respective picture elements of a received data flow of picture elements;
   sequentially determine whether adjacent picture elements of a row or a column of the data flow of picture elements are correlated by comparing the respective edge value, wherein picture elements are determined to be correlated if the edge value is the same;
   determine whether correlated elements in a row or a column is correlated with elements of a former row or column, respectively;
   connect such correlated elements into sub-regions of elements; and
   determine such sub-regions to be a potential glint.

4. The eye detection system according to claim 1, wherein said eye feature extraction module includes a pupil extraction module adapted to perform a pupil region extraction process on the received picture elements to identify picture elements including at least a part of a potential pupil region of an eye of the user, wherein said pupil extraction module is adapted, in said pupil extraction process, to:
   sequentially determine whether adjacent picture elements of a row or a column of the received at a flow of picture elements are correlated by comparing the respective intensity value, wherein two elements are determined to be correlated if the intensity values are within a predetermined interval;
   determine whether correlated elements in a row or a column is correlated with elements of a former row or column, respectively;
   connect such correlated elements into sub-regions of elements; and
   determine such sub-regions to be at least a potential pupil.

5. The eye detection unit according to claim 2, wherein said eye data generating module is adapted to generate eye data if the picture elements including at least a part of a potential pupil and the picture elements including at least a part of a potential glint is within a predetermined distance from each other in a sub-region.

6. The eye detection unit according to claim 5, wherein said eye data generating module is adapted to:
   map sub-regions determined to be at least a part of a potential pupil and sub-regions determined to be a potential glint to establish whether there is an overlap or close relation in distance; and
   if such an overlap or close relation in distance is established between at least a part of a potential pupil and at least one glint, then determine that the sub-regions including said at least a part of a potential pupil and said at least one glint constitute an eye.

7. The eye detection unit according to claim 1, wherein said eye data generating module is adapted use information about in which picture elements eye features were identified in a data flow at least one preceding digital image frame when identifying eye features in a data flow of a present digital image.

8. The eye detection unit according to claim 1, wherein said eye data generating module is adapted to send information to the image sensor instructing the sensor to forward picture elements of a data flow of at least one subsequent digital image frame that corresponds to picture elements in which eye features were identified in a data flow of a preceding digital image frame to at least one eye detection unit.

9. A method for detecting an eye using an eye detection system comprising at least one illuminator element adapted to emit light in a direction towards the head of a user; and at least one image sensor being adapted to receive light from the illuminated head of a user and repeatedly capture pictures, each picture being represented by a digital image frame comprising a matrix of picture elements, said method comprising the steps of:
providing selected data flows including at least one row or column of picture elements of a digital image frame divided in multiple data flows in parallel to a plurality of eye detection units;
performing parallel eye feature extraction processes on the received picture elements to identify predetermined eye features in said selected data flows in eye feature extracting modules, comprising
determining edge values of the respective picture elements of a received subset of picture elements, and
determining a potential glint by connecting picture elements of the subset having correlated edge values;
sending information of potential identified eye features from said eye detection units, said information including picture element coordinates for said identified eye features, and the received region of picture elements to an eye data generating module;
generating eye data based on said information of potential eye features, wherein said eye data is generated if identified eye features fulfil predetermined conditions; and
transferring generated eye data and the received regions of picture elements to a processing module, and wherein a data flow of said eye data and the region of picture elements of a digital image frame are substantially parallel.

10. The method according to claim 9, wherein the step of performing parallel eye feature extracting processes includes the steps of:
processing each intensity value of the picture elements of a received data flow of picture elements;
sequentially determining whether adjacent picture elements of a row or column of the data flow of picture elements are correlated by comparing the processed intensity value of said picture elements, wherein picture elements are determined to be correlated if the respective processed intensity value fulfils predetermined conditions;
determining whether correlated elements in a row or column is correlated with elements of a former row or column, respectively;
connecting such correlated elements into sub-regions of elements; and
determining such sub-regions to include potential eye features.

11. The method according to claim 9, wherein each eye feature extraction process includes a glint extraction process including the steps of:
performing an edge calculation to determine edge values of the respective picture elements of a received data flow of picture elements;
sequentially determining whether adjacent picture elements of a row or a column of the data flow of picture elements are correlated by comparing the respective edge value, wherein picture elements are determined to be correlated if the edge value is the same;
determining whether correlated elements in a row or a column is correlated with elements of a former row or column, respectively;
connecting such correlated elements into sub-regions of elements; and
determining such sub-regions to be a potential glint.

12. The method according to claim 9, wherein said eye feature extraction process includes a pupil extraction process including the steps of:
sequentially determining whether adjacent picture elements of a row or column of the received data flow of picture elements are correlated by comparing the respective intensity value, wherein two elements are determined to be correlated if the intensity values are within a predetermined interval;
determining whether correlated elements in a row or column is correlated with elements of a former row or column, respectively;
connecting such correlated elements into sub-regions of elements; and
determining such sub-regions to be at least a potential pupil.

13. The method according to claim 10, wherein said eye data generating step includes generating eye data if the picture elements including at least a part of a potential pupil and the picture elements including at least a part of a potential glint is within a predetermined distance from each other in a sub-region.

14. The method according to claim 13, wherein said eye data generating step includes the steps of:
mapping sub-regions determined to be at least a part of a potential pupil and sub-regions determined to be a potential glint to establish whether there is an overlap or close relation in distance; and
if such an overlap or close relation in distance is established between at least a part of a potential pupil and at least one glint, then determine that the sub-regions including said at least a part of a potential pupil and said at least one glint constitute an eye.

15. The method according to claim 9, wherein said eye data generating step includes the step of using information about in which picture elements eye features were identified in a data flow at least one preceding digital image frame when identifying eye features in a data flow of a present digital image.

16. The method according to claim 9, further including the steps of controlling said the image sensor to forward picture elements of a data flow of at least one subsequent digital image frame that corresponds to picture elements in which eye features were identified in a data flow of a preceding digital image frame to at least one eye detection unit.

17. An eye detection system comprising:
a plurality of eye detection units connectable to at least one image sensor being adapted to receive light from the illuminated head of a user and repeatedly capture pictures, each being represented by a digital image frame comprising a matrix of picture elements, said eye detection units being adapted to receive data flows including at least one row or column of picture elements of a digital image frame divided in multiple data flows substantially in parallel and wherein said eye detection units are adapted to operate substantially in parallel, each eye detection unit being adapted to receive a selected data flow of the picture elements of at least one digital image frame and including an eye feature extraction module adapted to perform a eye feature extraction process on the received picture elements to identify predetermined eye features; and an eye data generating module connected to said eye detection units and being adapted to:
  receive information of potential identified eye features from said eye detection units, said information including picture element coordinates for said identified eye features, and the received region of picture elements,
  generate eye data based on said information of potential eye features, wherein said eye data is generated if identified eye features fulfil predetermined conditions, and
  transfer generated eye data and the received regions of picture elements to a processing module, and wherein a data flow of said eye data and the region of picture elements of a digital image frame is substantially parallel; and said eye feature extraction module comprising a glint extraction module adapted to perform a glint extraction process on the received picture elements to identify picture elements including at least a part of a potential glint of an eye of the user, with said glint extraction module being configured to
  determine edge values of the respective picture elements of a received subset of picture elements, and
  determine a potential glint by connecting picture elements of the subset having correlated edge values.

18. The eye detection system according to claim 17, wherein said eye feature extraction module is adapted to:
  process each intensity value of the picture elements of a received data flow of picture elements;
  sequentially determine whether adjacent picture elements of a row or column of the data flow of picture elements are correlated by comparing the processed intensity value of said picture elements, wherein picture elements are determined to be correlated if the respective processed intensity value fulfils predetermined conditions;
  determine whether correlated elements in a row or a column is correlated with elements of a former row or column, respectively;
  connect such correlated elements into sub-regions of elements; and
  determine such sub-regions to include potential eye features.

19. The eye detection system according to claim 17, wherein said eye feature extraction module includes a glint extraction module adapted to perform a glint extraction process on the received picture elements to identify picture elements including at least a part of a potential glint of an eye of the user, wherein said glint extraction module is adapted, in said glint extraction process, to:
  perform an edge calculation to determine edge values of the respective picture elements of a received data flow of picture elements;
  sequentially determine whether adjacent picture elements of a row or a column of the data flow of picture elements are correlated by comparing the respective edge value, wherein picture elements are determined to be correlated if the edge value is the same;
  determine whether correlated elements in a row or a column is correlated with elements of a former row or column, respectively;
  connect such correlated elements into sub-regions of elements; and
  determine such sub-regions to be a potential glint.

20. The eye detection system according to claim 17, wherein said eye feature extraction module includes a pupil extraction module adapted to perform a pupil region extraction process on the received picture elements to identify picture elements including at least a part of a potential pupil region of an eye of the user, wherein said pupil extraction module is adapted, in said pupil extraction process, to:
  sequentially determine whether adjacent picture elements of a row or a column of the received data flow of picture elements are correlated by comparing the respective intensity value, wherein two elements are determined to be correlated if the intensity values are within a predetermined interval;
  determine whether correlated elements in a row or a column is correlated with elements of a former row or column, respectively;
  connect such correlated elements into sub-regions of elements; and
  determine such sub-regions to be at least a potential pupil.

21. The eye detection unit according to claim 18, wherein said eye data generating module is adapted to generate eye data if the picture elements including at least a part of a potential pupil and the picture elements including at least a part of a potential glint is within a predetermined distance from each other in a sub-region.

22. The eye detection unit according to claim 21, wherein said eye data generating module is adapted to:
  map sub-regions determined to be at least a part of a potential pupil and sub-regions determined to be a potential glint to establish whether there is an overlap or close relation in distance; and
  if such an overlap or close relation in distance is established between at least a part of a potential pupil and at least one glint, then determine that the sub-regions including said at least a part of a potential pupil and said at least one glint constitute an eye.

23. The eye detection unit according to claim 17, wherein said eye data generating module is adapted use information about in which picture elements eye features were identified in a data flow at least one preceding digital image frame when identifying eye features in a data flow of a present digital image.

24. The eye detection unit according to claim 17, wherein said eye data generating module is adapted to send information to the image sensor instructing the sensor to forward picture elements of a data flow of at least one subsequent digital image frame that corresponds to picture elements in which eye features were identified in a data flow of a preceding digital image frame to at least one eye detection unit.

* * * * *